(12) United States Patent
Titus et al.

(10) Patent No.: US 7,897,108 B1
(45) Date of Patent: Mar. 1, 2011

(54) SENSOR AND METHOD OF SENSING HAVING AN ENERGY SOURCE AND DETECTOR ON THE SAME SIDE OF A SENSOR SUBSTANCE

(75) Inventors: Albert H. Titus, Buffalo, NY (US); Frank V. Bright, Williamsville, NY (US); Alexander N. Cartwright, Williamsville, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 1010 days.

(21) Appl. No.: 10/957,254

(22) Filed: Oct. 1, 2004

Related U.S. Application Data

(60) Provisional application No. 60/508,758, filed on Oct. 3, 2003.

(51) Int. Cl.
*G01N 21/77* (2006.01)
*B32B 5/02* (2006.01)

(52) U.S. Cl. ............. 422/82.07; 422/82.08; 422/82.05; 422/68.1; 436/164; 436/170; 436/172

(58) Field of Classification Search ............. 422/82.05, 422/82.07, 82.08, 52, 68.1, 99, 55, 57; 436/164, 436/170, 172
See application file for complete search history.

(56) References Cited

U.S. PATENT DOCUMENTS

| | | | |
|---|---|---|---|
| 5,157,262 A * | 10/1992 | Marsoner et al. | 250/458.1 |
| 6,331,438 B1 * | 12/2001 | Aylott et al. | 436/172 |
| 6,379,969 B1 * | 4/2002 | Mauze et al. | 436/68 |
| 6,492,182 B1 * | 12/2002 | Bright et al. | 436/172 |
| 6,657,234 B1 * | 12/2003 | Tanizawa | 257/79 |
| 7,267,797 B1 * | 9/2007 | Craighead et al. | 422/82.05 |

* cited by examiner

*Primary Examiner*—Jill Warden
*Assistant Examiner*—Cedric Chan
(74) *Attorney, Agent, or Firm*—Hodgson Russ LLP

(57) ABSTRACT

A sensor has a sensor substance, an electromagnetic energy source, and a detector. The sensor substance may be able to emit electromagnetic energy different than that provided by the energy source when an analyte of interest is in contact with the sensor substance and electromagnetic energy is received by the sensor substance. The energy source and the detector may be provided on the same side of the sensor substance.

In a method according to the invention, a determination may be made as to whether an analyte is present in a sample. Such a method may provide a sensor, such as that described above. Electromagnetic energy may be provided to the sensor substance using the energy source, and the sensor substance may be contacted with a sample. Electromagnetic energy may be emitted from the sensor substance and received at the detector. The detector may provide a signal indicating the type of electromagnetic energy emitted from the sensor substance. The signal from the detector may be analyzed to determine whether the analyte was detected.

13 Claims, 7 Drawing Sheets

SENSOR AND METHOD OF SENSING HAVING AN ENERGY SOURCE AND DETECTOR ON THE SAME SIDE OF A SENSOR SUBSTANCE

CROSS-REFERENCE TO RELATED APPLICATION

This application claims the benefit of priority to U.S. provisional patent application Ser. No. 60/508,758, filed on Oct. 3, 2003.

FIELD OF THE INVENTION

The present invention relates to sensors and methods capable of detecting the presence of an analyte in a sample.

BACKGROUND OF THE INVENTION

Existing optically-based sensors have a configuration whereby the optically activated sensor substance resides between an optical pump and a detector. FIG. 1 depicts such an optically-based sensor. The optical pump is often a light emitting diode ("LED") or laser. The detector is often an array of detectors, such as a charge coupled device (often referenced as a "CCD"). FIG. 1 shows an example of such a prior art device. A sample to be analyzed is placed in contact with the sensor substance, and the light emitted from the sensor substance is received by the detector. The detector then sends a signal which may be analyzed to determine whether the sensor substance detected the analyte.

This geometry has advantages, but does not allow easy integration within a liquid environment. For example, the optical pump and the detector each may need to be independently sealed to protect them from a sample being analyzed. It would be better if the optical pump and the detector could be sealed as a single unit. Further, a frame is often employed to maintain the distance between the sensor substance and the detector. Requiring such a frame adds to manufacturing cost and may result in the sensor being relatively large.

SUMMARY OF THE INVENTION

The present invention includes a sensor having a sensor substance, an electromagnetic energy source, and a detector. The sensor substance may be able to emit electromagnetic energy, different than that provided by the energy source, when an analyte of interest is in contact with the sensor substance and electromagnetic energy is received by the sensor substance. The energy source and the detector may be provided on the same side of the sensor substance.

In a method according to the invention, a determination may be made as to whether an analyte is present in a sample. Such a method may provide a sensor, such as that described in the immediately prior paragraph. Electromagnetic energy may be provided to the sensor-substance using the energy source, and the sensor substance may be contacted with a sample. Electromagnetic energy may be emitted from the sensor substance and received at the detector. The detector may provide a signal indicating the type of electromagnetic energy emitted from the sensor substance. The signal from the detector may be analyzed to determine whether the analyte was detected.

BRIEF DESCRIPTION OF THE DRAWINGS

For a fuller understanding of the nature and objects of the invention, reference should be made to the accompanying drawings and the subsequent description. Briefly, the drawings are.

FURTHER DESCRIPTION OF THE INVENTION

Figure 1:
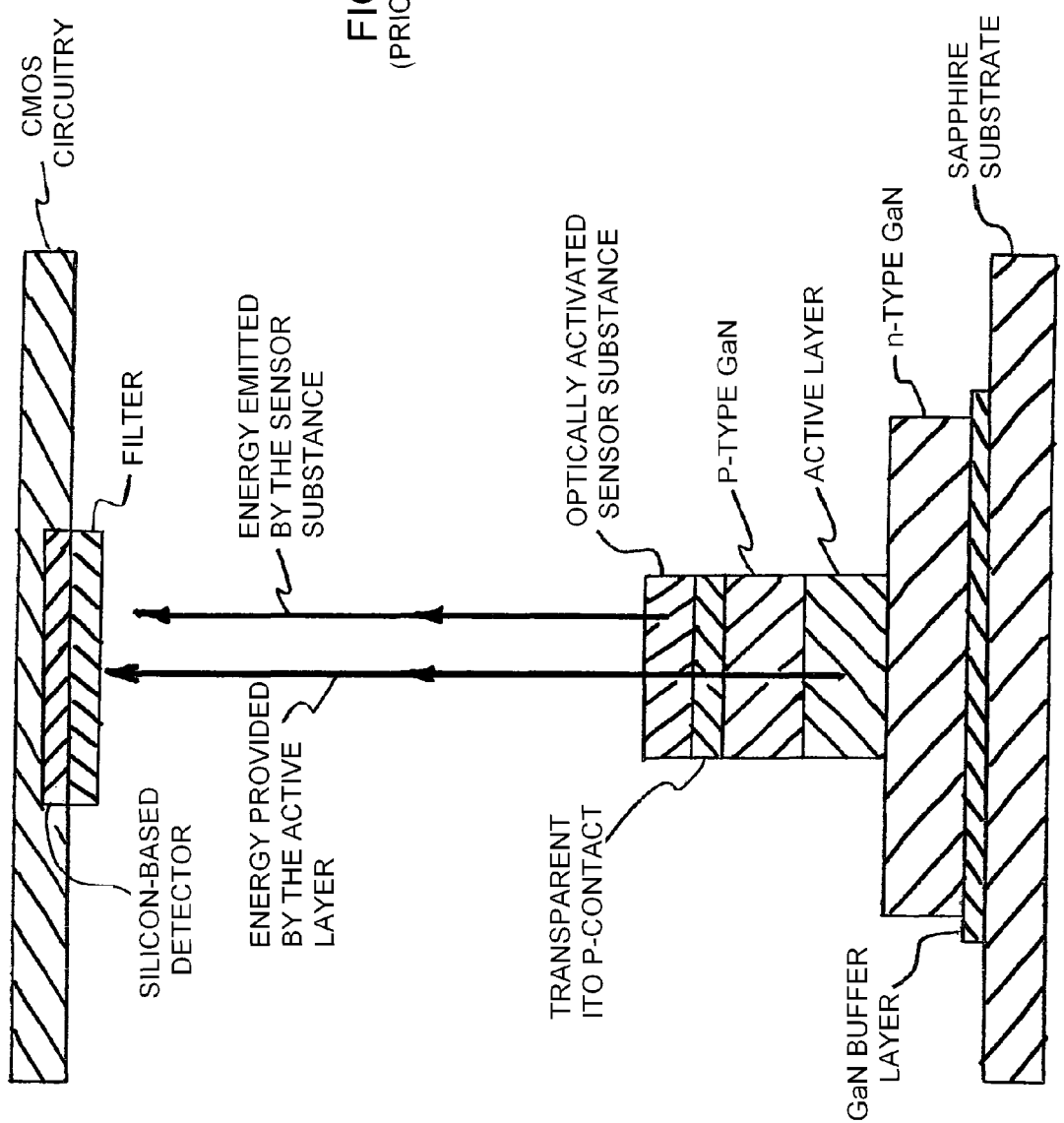
FIG. 1, which is a cross sectional diagram depicting a prior art device.
Figure 2:
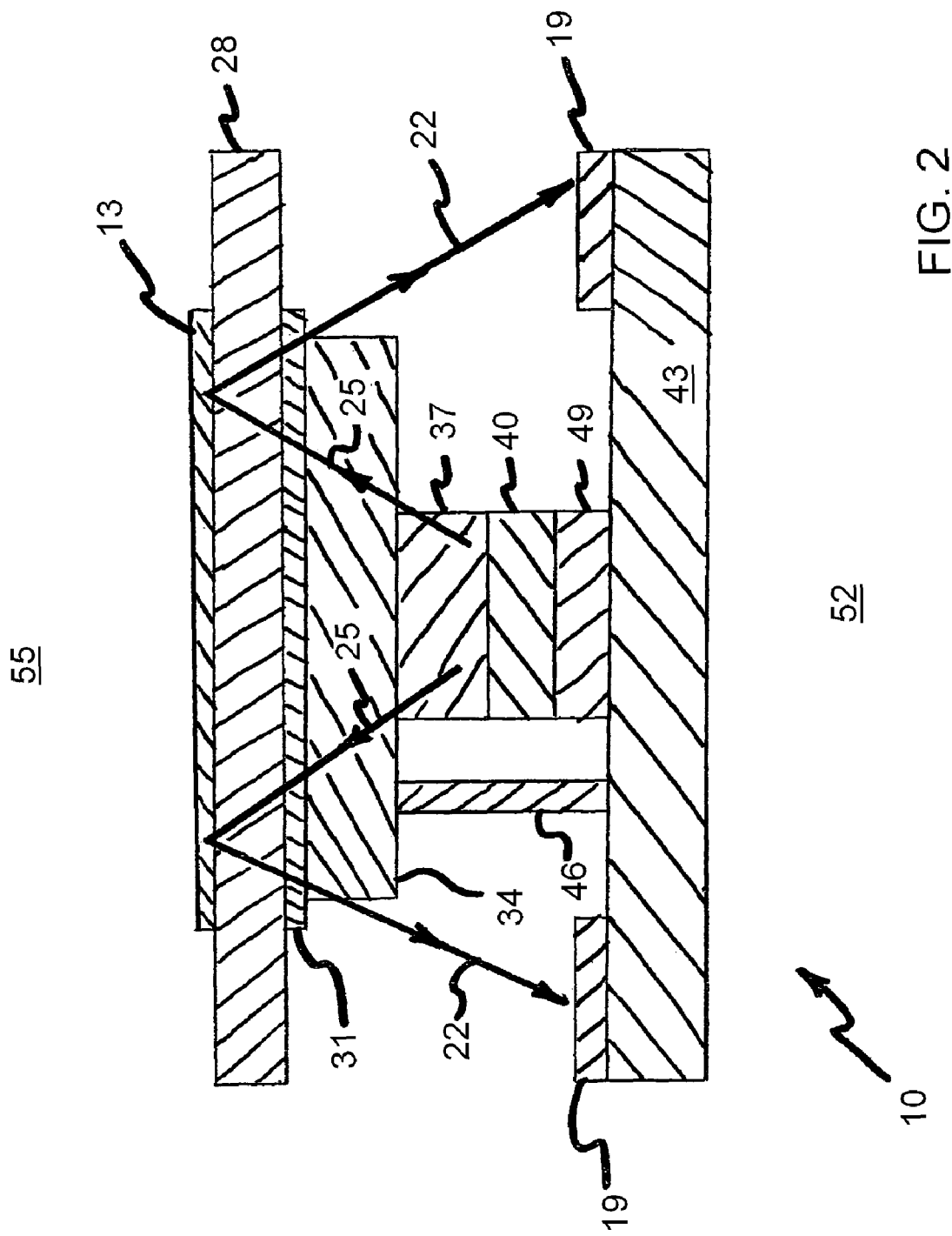
FIG. 2, which is a cross sectional diagram depicting a device according to the invention.
Figure 3:
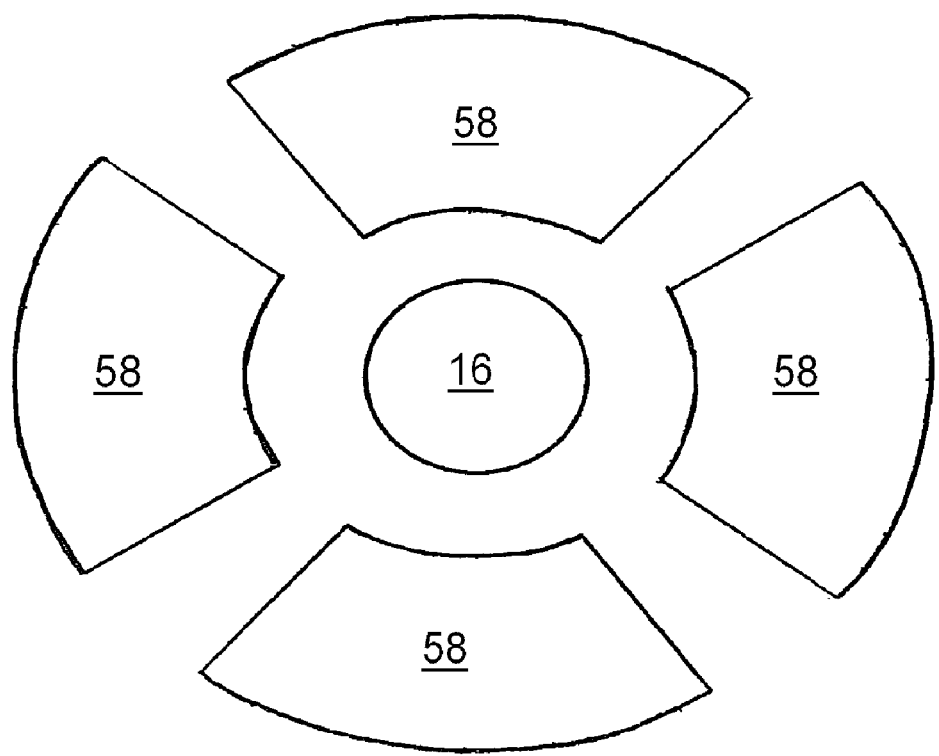
FIG. 3, which is a plan view diagram depicting an arrangement of the energy emitter and the detector according to the invention.

FIGS. 2 and 3 depict an embodiment of the invention. In FIGS. 2 and 3, there is shown a sensor 10 having a sensor substance 13, an energy source 16 and a detector 19. The sensor substance 13 may be able to emit electromagnetic energy 22 when an analyte of interest is in contact with the sensor substance 13 and electromagnetic energy 25 from the energy source 16 is received by the sensor substance 13. The emitted electromagnetic energy 22 may be different than the energy 25 provided by the energy source 16. For example, in the presence of the analyte of interest and the electromagnetic energy 25 from the energy source 16, the sensor substance 13 may exhibit characteristics that are not present when either the analyte or the electromagnetic energy 25, or both, are not present. In one embodiment of the invention, the sensor substance 13 may fluoresce when the analyte is present and electromagnetic energy 25 from the energy source 16 is provided to the sensor substance 13. There are many such sensor substances 13, and some of them may be purchased from Sigma-Aldrich, Inc. The amount of fluorescence from a given sensor substance 13 may be a function of the concentration of the analyte in the sample.

The energy source 16 may be a light emitting diode ("LED"). The LED may be a Galium-nitride ("GaN") based LED which was formed on a sapphire substrate 28. Such an LED may be constructed by forming a Galium-nitride buffer layer 31 on the sapphire substrate 28, forming an n-type GaN layer 34 on the buffer layer 31, forming an active layer 37 on the n-type GaN layer 34, and forming a p-type GaN layer 40 on the active layer 37. Techniques of forming such an LED are known, and therefore are not discussed in this document. The active layer 37 may be an Indium-galium-nitride/galium nitride ("InGaN/GaN") type.

The n-type GaN layer 34 may be connected to an electric circuit 43 via an N-contact 46, and the p-type GaN layer 40 may be connected to the electric circuit 43 via a P-contact 49. The electric circuit 43 may serve to control whether the LED is turned on to provide electromagnetic energy 25, or turned off. The electric circuit 43 may include CMOS transistors arranged to control, drive or modulate the LED and to process a signal provided by the energy detector 19. Processing of the signal provided by the energy detector 19 may include determining the brightness of the sensor substance 13, in order to determine the concentration of the analyte in the sample.

The invention is not limited to a GaN based LED. The energy source 16 may be an LED of a different type than that described above, and the energy source 16 need not be an LED. Further, the invention is not limited to an arrangement in which only one LED is used. More than one energy source 16 may be used. For example, different types of LEDs may be used in order to provide energy 22 to different types of sensor substances 13 so that a sensor 10 according to the invention may be used to detect different analytes.

The energy source 16 and detector 19 may be positioned on the same side of the sensor substance 13. For purposes of describing the invention, the "first side" 52 will be the side of the sensor substance 13 on which the energy source 16 and detector 19 reside. The "second side" 55 will be the side of the sensor substance 13 that contacts a sample to be analyzed for the presence of the analyte. In such an arrangement, the energy source 16 and the detector 19 may be sealed as a single unit in order to protect these components from a sample to be analyzed. Further, the energy source 16, sensor substance 13, and detector 19 may be formed as an integral unit, thereby eliminating the need for a frame to maintain the distance between the sensor substance 13 and the detector 19.

The energy detector 19 may be a silicon-based detector, for example, a CMOS optical detector. Such a detector 19 may be able to detect the presence of electromagnetic energy impinging a surface of the detector 19. The energy detector 19 may have more than one detector pad 58. The detector pads 58 may be located around the energy source 16 so as to receive electromagnetic energy 22 emitted by the sensor substance 13. In this manner, the energy source 16 may be centrally located relative to the detector pads 58. In a different arrangement according to the invention, more then one energy source 16 may be provided, and the energy sources 16 may be positioned around the detector 19 so that the detector 19 is centrally located with respect to the energy sources 16.

Figure 4:
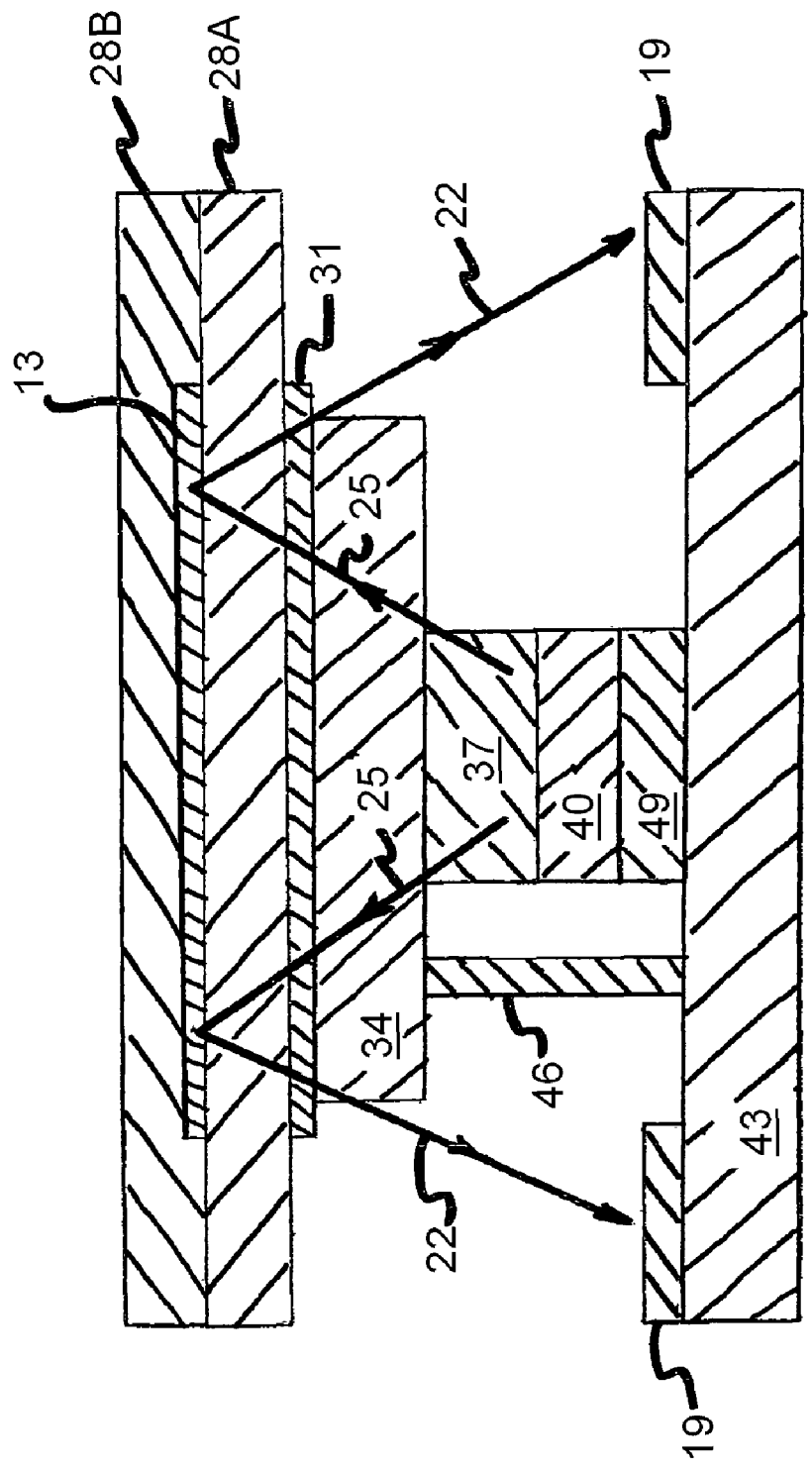
FIG. 4, which is a cross sectional diagram depicting a device according to the invention.
Figure 5:
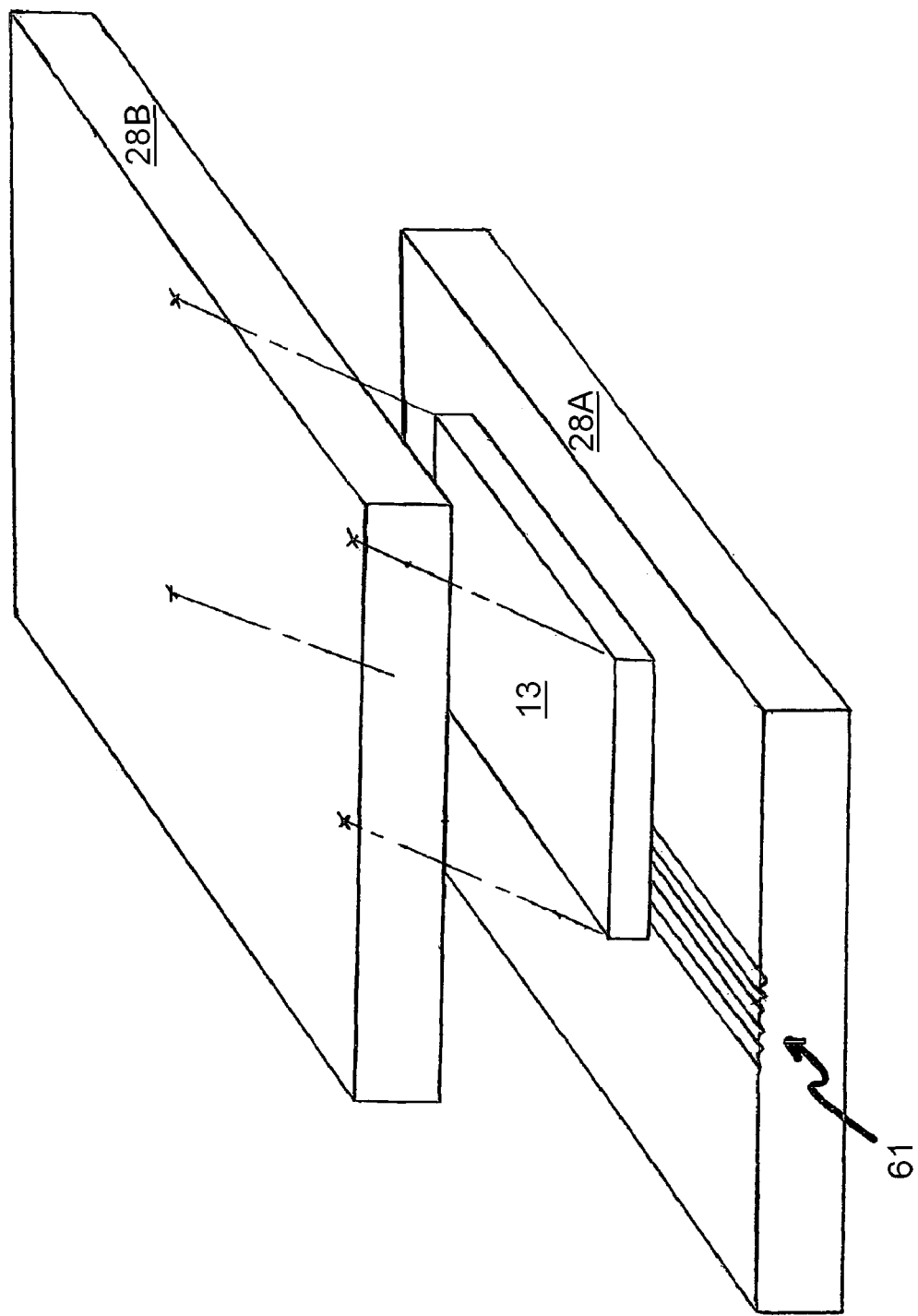
FIG. 5, which is a perspective view diagram depicting the two-piece substrate and a sensor substance of FIG. 4.

FIGS. 4 and 5 show an embodiment of the invention in which the sensor substance 13 resides in a substrate 28, such as the sapphire substrate 28 identified above. Channels 61 may be provided in the substrate 28 in order to convey a sample to the sensor substance 13. The channels 61 may be sized to control the volume of the sample and provide time for the sensor substance 13 to react to the presence of the analyte. The channels 61 may be formed by etching a first portion of the substrate 28A and sandwiching the sensor substance 13 between the first portion of the substrate 28A and a second portion of the substrate 28B.

More than one sensor substance 13 may be provided in a sensor 10 according to the invention. For example, a first sensor substance responsive to the presence of a first analyte and a second sensor substance responsive to the presence of a second analyte may be included in the same sensor 10. The energy source 16, which may include more than one type of LED, may be used to provide electromagnetic energy 25. The detector 19 may be fashioned to detect electromagnetic energy 22 emitted from both sensor substances 13, for example, the detector 19 may include a detector pad 58 that is able to detect electromagnetic energy 22 emitted from both sensor substances 13, or the detector 19 may include a first detector pad, which is able to detect energy 22 emitted from the first sensor substance and a second detector pad which is able to detect energy 22 emitted from the second sensor substance. In this manner, a single sensor 10 may be able to detect the presence of more than one analyte.

The sensor substance 13 may be part of a xerogel that is responsive to the analyte of interest. Methods of forming the sensor substances 13 on a surface may include those disclosed by E. J. Cho, F. V. Bright, "Integrated Chemical Sensor Array Platform Based on a Light Emitting Diode, Xerogel-Derived Sensor Elements, and High-Speed Pin Printing," Analytica Chimica Acta, vol. 470, pp. 101-110, 2002).

Figure 6:
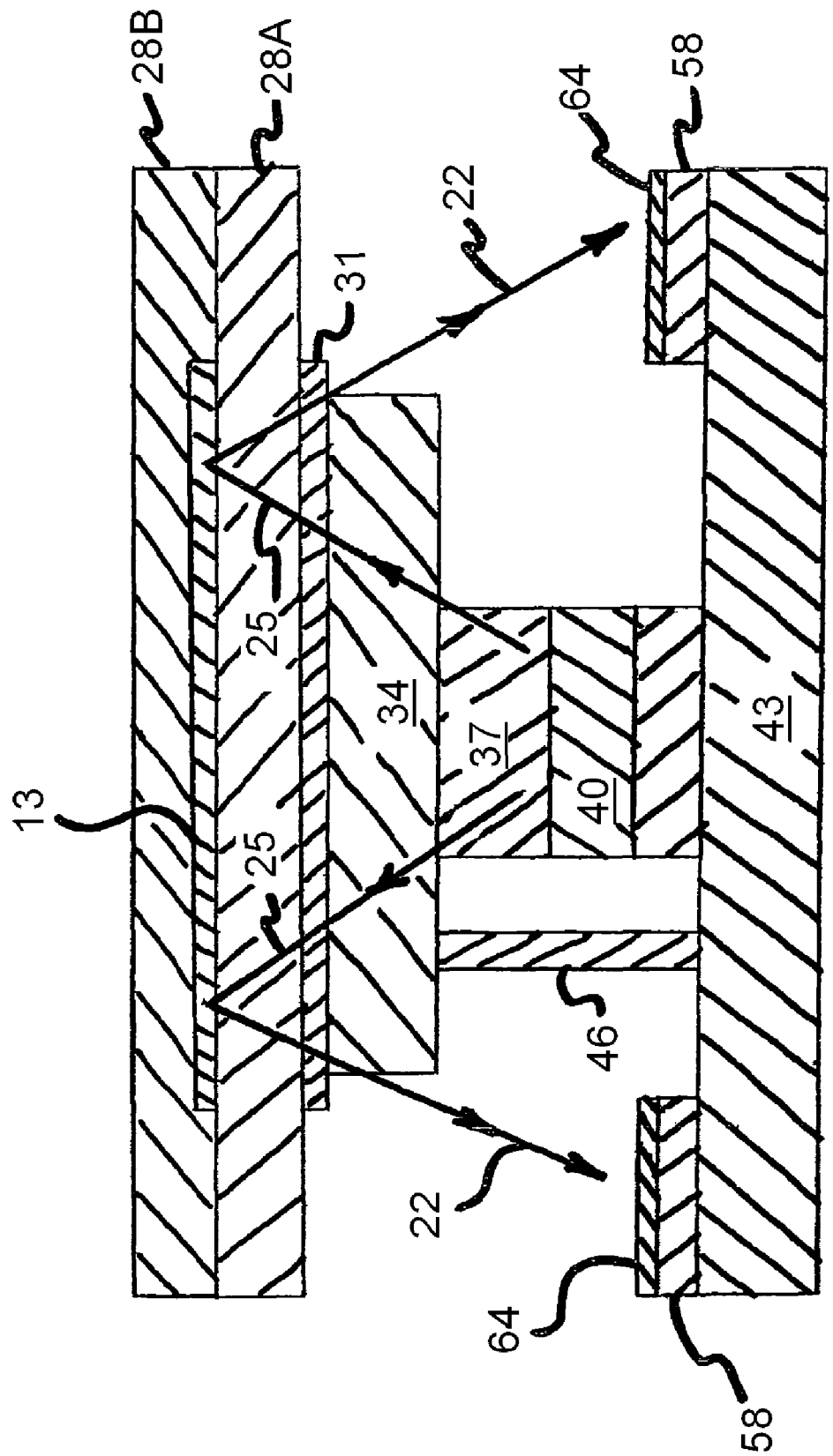
FIG. 6, which is a cross section diagram similar to that of FIG. 2, but showing a filter.
Figure 7:
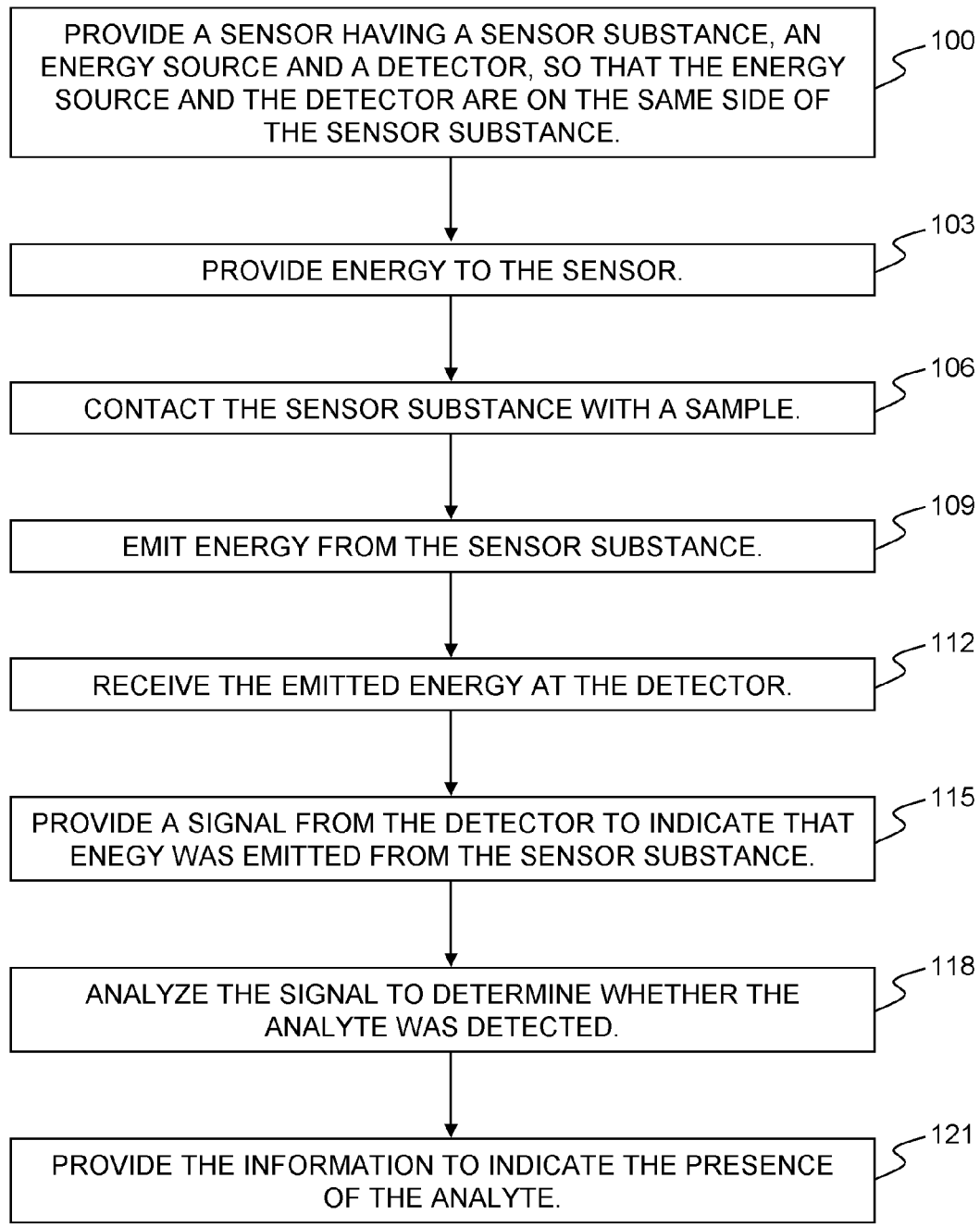
FIG. 7, which depicts a method according to the invention.

A filter 64 may be included in a sensor 10 according to the invention. FIG. 6 depicts such a sensor 10. The filter 64 may be provided to reduce or eliminate certain wavelengths that may interfere with the detector's 19 ability to determine whether the sensor substance 13 indicates the presence of the analyte. For example, the filter 64 may be provided to reduce or eliminate one or more wavelengths of electromagnetic energy 25 provided by the energy source 16. The filter 64 may be tunable so as to provide the ability to reduce or eliminate different wavelengths at different times.

In a method according to the invention, a determination may be made as to whether an analyte is detected in a sample. Such a method may begin by providing 100 a sensor having a sensor substance, an electromagnetic energy source, and a detector. The energy source and the detector may be on the same side of the sensor substance. Using the energy source, electromagnetic energy may be provided 103 to the sensor substance. The sensor substance may be contacted 106 with a sample, which may include the analyte. In the presence of energy from the energy source and the analyte, the sensor substance may emit 109 electromagnetic energy. The emitted energy may be received 112 at the detector, and the detector may respond by providing 115 a signal. The signal may indicate that electromagnetic energy was emitted from the sensor substance. The signal may be analyzed 118 by a receiver to determine whether the analyte was detected, and information may be provided 121 by the receiver to an individual in order to indicate the presence or absence of the analyte.

Although the present invention has been described with respect to one or more particular embodiments, it will be understood that other embodiments of the present invention may be made without departing from the spirit and scope of the present invention. Hence, the present invention is deemed limited only by the appended claims and the reasonable interpretation thereof.

What is claimed is:

1. A sensor, comprising:
   a sensor substance having a first side and a second side, the sensor substance being able to emit electromagnetic energy when an analyte of interest is in contact with the sensor substance and electromagnetic energy is received by the sensor substance;
   an electromagnetic energy source on the first side, the electromagnetic energy source being capable of emitting light;
   an emitted electromagnetic energy detector on the first side; wherein the sensor substance resides within a substrate, and the substrate includes a channel proximate to the sensor substance, the channel being able to convey a sample to the sensor substance; and
   wherein electromagnetic energy emitted from the sensor substance is received by the energy detector without transmission through the electromagnetic energy source.

2. The sensor of claim 1, wherein the source is a light emitting diode.

3. The sensor of claim 2, wherein the light emitting diode includes Gallium-nitride.

4. The sensor of claim 3, wherein the light emitting diode includes an n-type Gallium-nitride layer, an active layer, and a p-type Gallium-nitride layer.

5. The sensor of claim 4, wherein the n-type Gallium-nitride layer is formed on a Gallium-nitride buffer layer, and the buffer layer is formed on a sapphire substrate.

6. The sensor of claim 4, wherein the active layer includes Indium-gallium-nitride.

7. The sensor of claim 6, wherein the active layer further includes Gallium-nitride.

8. The sensor of claim 1, wherein the energy detector is a silicon detector.

9. The sensor of claim 1, wherein the energy detector is comprised of at least two detector pads.

10. The sensor of claim 9, wherein the energy source is centrally located relative to the detector pads.

11. The sensor of claim 1, wherein the energy source is comprised of at least two light emitting diodes.

12. The sensor of claim 11, wherein the detector is centrally located relative to the light emitting diodes.

13. The sensor of claim 1, wherein the sensor substance includes a xerogel having a sensor compound that is responsive to the analyte.

* * * * *